United States Patent [19]

Pittman

[11] Patent Number: 4,466,951

[45] Date of Patent: Aug. 21, 1984

[54] INTRACELLULAR TRAPPING OF THERAPEUTICS OR TRACER AGENTS

[75] Inventor: Ray C. Pittman, Del Mar, Calif.

[73] Assignee: University of California, Berkeley, Calif.

[21] Appl. No.: 441,275

[22] Filed: Nov. 12, 1982

[51] Int. Cl.$^3$ .................. A61K 43/00; A61K 49/00
[52] U.S. Cl. .................. 424/1.1; 260/112 R; 536/1.1; 424/9
[58] Field of Search .................. 260/112 R; 536/1.1; 424/1.1, 9

[56] References Cited

U.S. PATENT DOCUMENTS

| | | | |
|---|---|---|---|
| 3,993,754 | 11/1976 | Rahman et al. | 424/177 |
| 4,157,323 | 6/1979 | Yen et al. | 424/1.1 |
| 4,385,046 | 5/1983 | Milbrath et al. | 424/1.1 |
| 4,386,026 | 5/1983 | Ponpipom et al. | 260/112.5 R |

FOREIGN PATENT DOCUMENTS 52-51032  4/1977  Japan .................. 424/177

OTHER PUBLICATIONS

Pittman et al., Biochem. J., vol. 212, (1983), pp. 791–800.

*Primary Examiner*—Christine M. Nucker
*Attorney, Agent, or Firm*—Poms, Smith, Lande & Rose

[57] ABSTRACT

A method is provided for trapping therapeutic or tracer agents within cells to maximize their therapeutic effect or detectability. Primary amine containing therapeutic or tracer agents are bound by reductive deamination to the active carbonyl of cellobiose. The resulting adduct is attached to a targeting agent for introduction into a selected cell. Due to the cellobiose, the adduct remains trapped within the cell to maximize therapeutic or tracer activity. Novel adducts and targeting agent-adduct conjugates are disclosed. A new double label method for measuring protein metabolism is also disclosed.

27 Claims, 1 Drawing Figure

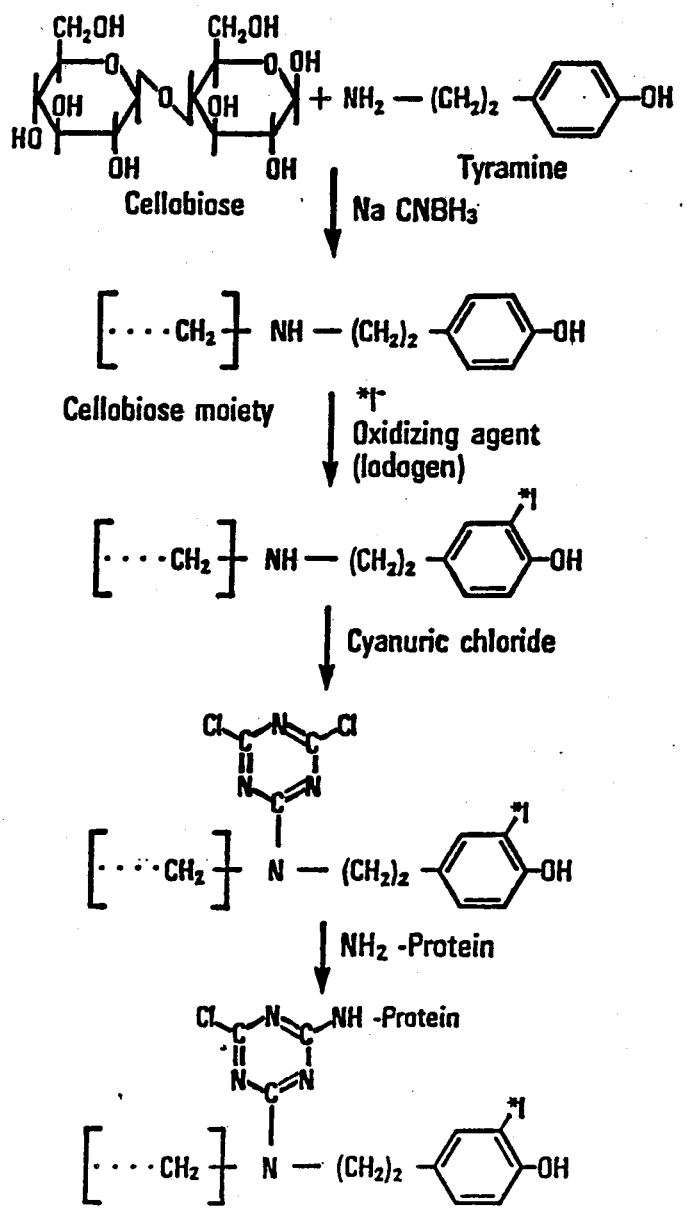

INTRACELLULAR TRAPPING OF THERAPEUTICS OR TRACER AGENTS

This invention was made with Government support under Grant Nos. HL 14197 and HL 22053 awarded by the Department of Health and Human Services. The Government has certain rights in this invention.

BACKGROUND OF THE INVENTION

The present invention relates generally to introducing therapeutic or tracer agents into selected cells and trapping the agents within the cells to optimize therapeutic activity or tracer detectability.

In many disease states, most obviously in various forms of cancer, it is desirable to target therapeutic and/or tracer agents to specific cell types. Two problems exist in such targeting. The first is to cause specific uptake of the radioisotope or other agent by the target cells. The second is to prevent the redistribution of the agent to other cells after uptake by the target cells to thereby optimize action of the agent.

Progress has been made on the first problem by attaching therapeutic or tracer agents to targeted proteins, e.g. monoclonal antibodies, glycoproteins which are targeted to specific cell receptors recognizing certain terminal carbohydrate moieties, etc. In each case, the targeted protein and attached therapeutic or tracer agent are incorporated into the target cell after binding to specific membrane elements.

Some progress has also been made regarding the second problem relating to the trapping of therapeutic or tracer agents once they are incorporated into the target cells.

For example, one approach to the problem of intracellular trapping arose from the long time use of a common disaccharide, sucrose, as a marker of fluid endocytosis. Once incorporated into cells by fluid endocytosis, sucrose is not metabolized since mammalian cells lack the necessary glycosidase. The sucrose is therefore effectively trapped within the cell since the sucrose is unable to cross cell membranes. The sucrose thus accumulates over time as a cummulative measure of fluid uptake. Taking advantage of these properties of sucrose, a technique was developed for determining the sites of degradation of plasma proteins by covalently attaching radiosucrose to the particular protein to be introduced into a cell for degradation (Pittman and Steinberg, 1978, Biochem. Biophys. Res. Commun. 81, 1254–1259; Pittman et al, 1979, J. Biol. Chem. 254, 6876–6879: Pittman et al, 1979, Proc. Natl. Acad. Sci. USA 76, 5345–5349). After injection of the tracer protein labeled with radiosucrose, the protein is degraded within the cells. The radiosucrose moiety is not degraded but remains trapped within those cells participating in uptake as a cummulative measure of degradation by those cells.

Although the above sucrose-based process has shown promise, it is limited to trapping only radiolabeled sucrose within the targeted cell. Since the $^{14}C$ and $^3H$ iostopes of sucrose are the only isotopes which are readily avilable, the method is limited in the possible radioisotopes of sucrose which can be introduced into cells as either therapeutic or tracer agents. Further, the adaptability of sucrose to carry separate therapeutic agents has not been demonstrated. There is therefore still presently a need to provide a method and trapping agent which is capable of trapping a wide variety of therapeutic and/or tracer agents within cells.

SUMMARY OF THE INVENTION

In accordance with the present invention, it was discovered that cellobiose can be used as a suitable trapping sugar in a manner similar to sucrose. It was further discovered that cellobiose may be linked by a nonmetabolzable bond to primary amine-containing therapeutic and tracer agents by reductive amination. The ability to link tracer and therapeutic agents to cellobiose by a nonmetabolizable bond provides a highly versatile method for trapping a wide variety of therapeutic and tracer agents within cells. The versatility of the present method is an improvement over sucrose based trapping procedures in which therapeutic and tracer agents are limited to radioisotopes of sucrose.

The present invention is based upon a method in which cellobiose is reductively aminated and bound by way of its active carbonyl to a suitable primary amine therapeutic or tracer agent. The resulting bond is a stable carbon-nitrogen bond between the cellobiose and tracer or therapeutic agent. This stable bond is not amenable to hydrolysis in cells so that the therapeutic or tracer agent remains attached to and trapped with the cellobiose upon introduction into a cell.

As a particular feature of the present invention, the adduct of cellobiose and primary amine-containing therapeutic or tracer agent is attached to a targeting agent to form a targeted adduct for selective introduction into particular cells. By varying the particular targeting agent, different target cells may be selectively treated or identified utilizing therapeutic or tracer agents in accordance with the present invention.

The present invention may be applied to a wide range of medical uses. For example, radioiodine-labeled tyramine may be attached to cellobiose and introduced into target cells utilizing a suitable targeting protein, such as an antibody or a fragment or derivative product of an antibody. Since radioiodine is readily available in at least four isotopic forms, the radioiodine used can be matched for the desired therapeutic or tracer effect. For example, high doses of beta emitting radioiodine may be included in the tyramine to kill cells into which the adduct is introduced. Lower doses of radioactivity may be used if imaging only of the target cells for identification is desired. More specifically, antibodies, antibody fragments or derivatives of antibodies specific for a tumor antigen can be coupled to the radioiodinated cellobiose-tyramine adduct and used to image tumors and metastasizing growths.

The present invention also has wide applications as a research tool for determining the cites of protein degradation in cells. Although the radiosucrose labeling technique mentioned in the Background of the Invention has been used for such investigations, the method of the present invention provides advantages over this technique due to the much higher specific activities obtainable (more than 100 X higher) and due to the wide variety of possible therapeutic or tracer agents which may be effectively trapped within cells. The above discussed and many other features and attendant advantages of the present invention will become apparent as the invention becomes better understood by reference to the following detailed description when considered in conjunction with the accompany drawing.

BRIEF DESCRIPTION OF THE DRAWING

The drawing is a schematic representation of an exemplary preparation of a targeted adduct in accordance with the present invention.

DETAILED DESCRIPTION OF THE INVENTION

The present invention basically involves attaching primary amine-containing therapeutic and/or tracer agents to cellobiose to form an intracellularly trappable nonmetabolizable adduct. This adduct is then attached to a suitable targeting agent which introduces the adduct into desired cells where the cellobiose is effective in retaining the therapeutic or trapping agent within the cell. The conjugated adduct and targeting agent are referred to hereinafter as a targeted adduct.

Cellobiose is a well known disaccharide sugar. Cellobiose is used as the trapping agent since it is a nonmetabolizable sugar with a reactive carbonyl group. This carbonyl group allows easy chemical manipulation and attachment of a wide variety of therapeutic and tracer agents. Attachment of these agents to the cellobiose is generally carried out by reductive amination in the presence of sodium cyanoborohydride or sodium borohydride. The mechanism of cellobiose reductive amination and bond formation to primary amines is well known.

A wide variety of therapeutic or tracer agents may be attached to the cellobiose. The agent preferably will have a primary amine group which can attach to the reactive carbonyl group present on cellobiose to produce a stable bond. Tyramine is a preferred agent. Suitable therapeutic or tracer agents include primary amine chelating agents capable of carrying radio-metals, such as $^{99m}$Tc and $^{111}$In for imaging and alpha, beta and positron emitters for therapy. An exemplary chelating agent suitable for carrying radio-metals for therapy or imaging is p-aminophenyl-ethylenedinitrilotetraacetic acid.

Any of the amino acids or amino sugars labeled with $^{14}$C, $^{3}$H, $^{35}$S or other known isotopes may suitably be employed. For example, radioiodine labeled tyrosine is a preferred therapeutic or tracer agent due to its close similarity to tyramine. Other possible therapeutic or imaging agents include compounds rich in $^{10}$B, such as 2-(p-aminophenyl)-1,2-dicarba-closo-dodecaborane. This particular radiotherapeutic compound decays on exposure to a neutron flux to yield alpha particles and lithium nuclei which inflict injury to cells in a localized manner. Thus cell injury can be confined to the time after uptake and trapping in cells.

Once the cellobiose-therapeutic or tracer agent adduct (adduct) is prepared, it must then be attached to a suitable targeting agent for introduction into selected cells. Various different targeting agents are widely known and used for attaching or introducing various desired therapeutic agents or tracers to selective cells. Targeting agents generally are proteins, but may also include smaller peptides and glycoproteins. The particular targeting agent or protein which is utilized is not particularly critical to the applicability of the trapping method since the binding mechanism between the adduct and protein is believed to apply for most proteins. Selection of the targeting agent will be based for the most part upon the desired cells into which the adduct is to be introduced. For example, monoclonal antibodies, or their fragments or derivatives, which are directed against specific cell surface components may be utilized. Such cell surface components include various antigenic sites such as the carcinoembryonic antigens found on some cancer cells. $F_{ab}$ fragments of antibodies may also be utilized. Synthetic peptides may also be used which are reactive with antigens on cell surfaces or specific cell surface receptors. Hormones or hormone analogs, such as insulin and adrenocorticotropic hormone may be used. Suitable targeting agents include proteins chemically derivatized so as to cause them to be targeted for specific cells. Suitable derivatized proteins include: asialoglycoproteins including asialofetuin and asialotransferrin; lactosylated proteins including lactosylated low density lipoprotein; acetylated and acetoacetylated proteins including acetylated or acetoacetylated low density lipoprotein; and maleylated proteins including maleylated albumin.

Carbohydrate targeting agents not having primary amine groups may also be suitably attached to cellobiose using a linking arm, as in the case of p-aminophenyl derivatives or other derivatives of sugars that provide an available primary amine. Also attachment of chains of mannose, mannose phosphate or the carbohydrate chains derived from asialotransferrin may be provided. Other possible targeting compounds include antibiotics such as bleomycin.

Linking or binding of the adduct to the targeting agent can be accomplished by any number of known conventional techniques. Linking agents which can be used include cyanuric chloride, dimethyl adipimidate, dimethyl pimelimidate, 1,5-difluoro-2,4-dinitrobenzene or p-phenylene diisothiocyanate.

Although any number of primary amine-containing therapeutic or tracer agents can be suitably attached to cellobiose by conventional reductive deamination, the following description will be limited to an example in which radiolabeled tyramine is used as a tracer agent. It will be realized that a description relating to tyramine can be applied, in general, to primary amine-containing therapeutic or tracer agents. Many details of the procedure for synthesis and purification of course will differ.

The overall method for synthesis, iodination and protein binding of the tyramine-cellobiose ligand is shown in the drawing. Tyramine was linked to cellobiose by reductive amination using NaBH$_3$CN to reduce the transient Schiff base, giving a stable carbon-nitrogen bond which is not amenable to hydrolysis in cells. Cellobiose, tyramine and NaBH$_3$CN were obtained from Sigma Chemical Co. The three reagents were solubilized at equimolar concentrations (0.12 M) in 0.2 M sodium phosphate buffer (4.55 g cellobiose, 1.82 tyramine and 0.83 g NaBH$_3$CN in 100 ml at pH 7.5). Tracer $^3$H tyramine (100 Ci) was added to facilitate later quantitation and identification of products.

The mixture was allowed to react for a total of 6 days at room temperature. It was then adjusted to pH 5.5 with HCl and applied to a column (2×20 cm) containing a strongly acidic cation exchange resin (Biorad AG-50W-X8) in the protonated form. The column was eluted with water (300–400 ml) and then with 0.5 M. NH$_4$OH. The material eluting with NH$_4$OH which contained the adduct and unreacted tyramine was lyophilized. The adduct and free tyramine were resolved by silicic acid chromatography on a 2×25 cm column eluted with butanol:acetic acid:water (70:10:20). Tyramine preceded the product from the column, eluting at about 50 ml. The major product eluted over the next 70 ml. The product was visualized by thin layer chromatography on silica gel developed in butanol:acetic acid:-water (70:10:20). The major product stained for both carbohydrate and amine moieties. This product was partially overlapped by a by-product also containing both carbohydrate and amine moieties that eluted beginning at about 90 ml. The region containing the major product, but excluding the more retained by-product, was pooled and lyophilized. Further purification was achieved by gel filtration on Sephadex G-10 which removed a lower molecular weight component. The final product displayed one predominant band on TLC with a small contaminant of slightly slower migration.

To quantitate the purity of the product, the two components were resolved by paper chromatography using the developing system described above and extracted from the paper. The UV spectra of these components were indistinguishable from each other and from that of free tyramine. Measurement of absorbance at the absorbance maximum (277 nm) disclosed 83% purity of the major component and 12% minor component, assuming equal extinction coefficients. The impurity is believed to be the product of reaction of 2 molecules of cellobiose with 1 molecule of tyramine, based on its staining behavior with carbohydrate and amine reagents. The amine group of tyramine in such a complex would not be available for further reaction.

The product was prepared free of the minor component by preparative TLC in the system outlined above and used in labeling studies. Alternatively, the product from silicic acid chromatography was more fully purified to yield a single component by chromatography on silicic acid eluted with chloroform:methanol:water:concentrated $NH_4OH$ (64:31:2:3). The behavior of the fully purified preparation and the less pure preparation were indistinguishable. The 83% pure preparation was stored at $-6°$ C. and used for the following examples.

The tyramine-cellobiose adduct was radioiodinated prior to its activation and binding to protein. Iodination was carried out using carrier-free radioiodide and a water-insoluble oxidizing agent (Iodogen, Pierce Chemical Co.). In the usual procedure a micro-reaction vessel was coated with 10 microgram Iodogen introduced in methylene chloride, which was evaporated gradually with hand warming. To the Iodogen-coated vessel was added 0.03 to 0.10 micro mole of the tyramine-cellobiose ligand in 3 to 10 microliters of 0.2 M sodium phosphate buffer, pH 7.2. The desired amount of Na*I (usually 2–5 mCi) was added and reaction was allowed to proceed for about 30 min. at room temperature.

After this final treatment, the mixture was transferred to a fresh vial containing 10 microliters of 0.1 M sodium bisulfite and 5 microliters of 0.1 M NaI to stop further reaction. The efficiency of iodination was generally 80–95%. This was determined by removing a trace amount of the reaction mixture to a tube containing unlabeled NaI at pH 5.0. $H_2O_2$ was added to oxidize the iodide to iodine, which was exhaustively extracted into $CHCl_3$. Radioiodine remaining in the aqueous phase was taken as a measure of adduct-bound radioiodine. The radioiodinated tyramine-cellobiose adduct was used without separation from residual radioiodide, NaI and sodium bisulfite.

The radioiodinated adduct was reacted with a cross-linking agent, cyanuric chloride, for binding to protein. To the 35 to 75 microliters of radioiodinated ligand was added 1 molar equivalent (0.03 to 0.10 micro mole) cyanuric chloride (2,4,6-trichloro-1,3,5-triazine) in 20 microliters acetone, and 2 molar equivalents (0.06–0.2 micro mole) NaOH in 5 microliters water. After 10–30 sec., 3 molar equivalents (0.09 to 0.3 micro mole) acetic acid in 5 to 20 microliters water was added to quench further reaction. The resulting activated ligand was used immediately for binding to protein, although reactivity was maintained for at least an hour. The proteins to which the activated ligands were bound included human low density lipoprotein (LDL), rabbit LDL, rat apo AI, asialofetuin, asialotransferrin, rabbit albumin and porcine insulin.

In the case of all proteins except low density lipoprotein (LDL), the activated ligand was added to an appropriate amount of protein in sodium phosphate buffer, pH 7.0–7.5. For these proteins, about 0.8 mole of ligand was added per mole of protein in order to obtain a product with no significant population of molecules carrying more than one ligand. Reaction was carried for at least one hour, at which time binding was near maximal. In the case of LDL, 1 mole of ligand was reacted per 100 mg LDL protein. Reaction was carried out for 20–30 minutes at pH 9.0, under conditions which minimized labeling of lipid moieties.

In all cases the labeled protein was made to 0.1 M $NH_4HCO_3$ and either dialyzed against 0.1 M $NH_4HCO_3$ or applied to appropriate gel filtration columns eluted with 0.1 M $NH_4HCO_3$. Columns were chosen to just exclude the protein. Exhaustive dialysis was then carried out against 0.154 M NaCl buffered with 0.02 M sodium phosphate (pH 7.4) and containing 1 mM EDTA. The efficiency of ligand binding to protein was generally >70%, determined in terms of the amount of radioiodine bound to protein, corrected for that fraction of radioactivity present as radioiodide. The extent of derivatization was always less than 1 tyramine-cellobiose residue per protein molecule, or, in the case of LDL, less than 1 residue per 100,000 daltons of LDL protein. Specific activity at the time of use of the preparations was generally 200–500 cpm/g protein. In the case of insulin, specific activity was 40,000 cpm/ng protein.

All final preparations of labeled proteins except LDL contained less than 1% *I soluble in 10% trichloracetic acid. LDL contained less than 2%, but a greater fraction of label was soluble in 50% tetramethylurea, a reagent which delipidates and specifically precipitates the apo B component of LDL. This was reduced to less than 5% under the labeling conditions outlined above for LDL.

Applicant believes that the tyramine-cellobiose ligand binds to lysine residues of proteins. This was studied using rabbit albumin labeled with the tyramine-cellobiose ligand set forth above. The derivatized protein was exhaustively hydrolyzed with pronase before separation of the glycopeptides by gel filtration and then by chromatography on a "boranate" affinity column (Biorad, Affigel 601). Examination of this product by thin layer chromatography and amino acid analysis indicated that lysine residues were the predominant sites of attachment.

Conventionally radioiodinated proteins were prepared for comparative purposes using carrier-free radioiodide and Iodogen as the oxidizing agent generally as outlined above for labeling the tyramine-cellobiose adduct. In some cases proteins were both directly iodinated and labeled by attachment of the tyramine-cellobiose ligand. In these cases direct iodination was carried out first to avoid possible labeling of the tyramine moiety with both iodine isotopes. About 5 mg protein was reacted with Na$^{131}$I or Na$^{125}$I (usually 1–3 mCi) in a tube coated with 10 microgram Iodogen at pH 7.0–7.5 (for LDL pH 9.5) for 30 min. (10 min. for LDL). Efficiency of iodination was generally 80–95%, as determined by precipitation by 10% trichloroacetic acid of a trace aliquot in carrier protein. If necessary, reaction was continued in a new vial coated with Iodogen. Labeling of the lipid component of LDL was about 3%. It was found that LDL labeled in this manner was not distinguished from LDL labeled by the ICl method (McFarlane, A. S. (1958) Nature 182, 53), either in competition experiments in cultured human fibroblasts, or in terms of plasma decay curves in rabbits after the simultaneous intravenous injection of LDL directly radioiodinated by the two methods.

The various proteins to which the activated ligands were attached were prepared by conventional techniques. Human LDL, d 1.02–1.06, was isolated by sequential ultracentrifugation using NaBr to adjust solution density. Rat apo Al was prepared from rat high density lipoprotein, d 1.12–1.21 as reported in detail elsewhere (Glass, C. K., Pittman, R. C. and Steinberg, D. (1982) Submitted to J. Biol. Chem.). Fetuin and transferrin were purchased from Sigma Chemical Co. and desialytated using neuraminidase immobilized on agarose beads as previously described (Artie, A. D., Pittman, R. C. and Steinberg, D. (1980) Proc. Natl. Acd. Sci. USA 77, 5923–5927).

In vivo examples

Indwelling catheters were placed in the external jugular veins of experimental rats and rabbits under general anesthesia the day before beginning experimental protocols. Catheters were used for injection of labeled proteins and for withdrawal of blood samples to determine plasma decay kinetics. The kinetics were determined in terms of trichloroacetic acid precipitable label present in plasma during the time course. At termination of the experiments, animals were killed and tissues taken for radioassay as described earlier (Pittman, R. C., Artie, A. D., Careu, T. E. and Steinberg, D. (1982) Biochem. Biophys., Acta 710, 7–14; Pittman, R. C., Careu, T. E., Artie, A. D. Witztum, J. L., Watanabe, Y. and Steinberg, D. (1982) J. Biol. Chem. 275, 7994–800). In most experiments tissue pieces were placed directly into tubes for radioassay. About 1 g samples were used, compressed in the bottoms of the tubes to a volume of about 1 ml. Where indicated in the discussion of results, radioiodine was measured in tissue homogenates, generally 1.5 (W:V) in water. Protein-bound radioiodine in these homogenates was determined after precipitation with 10% trichloroacetic acid.

In all cases when determining both $^{115}$I and $^{131}$I, appropriate window settings of the gamma scintillation counter and correction factors were used to separate decay spectra of the two isotopes.

Plasma decay data were analyzed as previously described (Careu, T. E., Pittman, R. C. and Steinberg, D. (1982) J. Biol. Chem. 257, 8001–8007). All curves were adequately fit with computer aid to biexponential functions. Fractional catabolic roles were determined according to the treatment of Matthews (Matthews, C. M. E. (1957) Phys. Med. Biol. 2 36–53).

Studies of LDL catabolism in cultured human fibroblasts were carried out as previously described (Pittman, R. C., Green, S. R., Artie, A. D. and Steinberg, D. (1929) J. Biol. Chem. 254 6876–6879). Cells were incubated in lipoprotein-deficient serum for 24 hr. before addition of labeled lipoprotein. Degradation of both the conventionally iodinated proteins and those labeled with the tyramine-cellobiose ligand was calculated as the sum of total cell-associated radioactivity after trypsin treatment of the cells, plus that appearing in the medium as radioiodide soluble in 10% trichloroacetic acid.

The exemplary studies outlined below are directed toward demonstrating the use of the trapped adduct attached to a protein as a tool in determining the sites of degradation of that protein in experimental animals. It will be recognized that the criteria justifying this use are those necessary to justify the use of the desired adduct and analagous adducts for purposes of trapping therapeutic agents or of enhancing radiological imaging. In all these cases the primary requirements are that the protein derivatized by attachment of the adduct be recognized as the native protein, and that there be adequate trapping of the adduct ensuing from that uptake with no significant redistribution of the tracer, therapeutic agent and imaging agent between cells.

Derivatization of human LDL with the tyramine-cell-obiose (TC) ligand did not alter its recognition and uptake by the cultured human fibroblasts, and the ligand was well trapped on degradation of the protein. The retention of TC-labeled LDL ([$^{125}$I-TC]-LDL) and directly iodinated LDL ($^{131}$I-LDL) by cultured human fibroblasts was compared during exposure to the labeled LDL's for 24 hr. Radioactivity in catabolic products from $^{131}$I-LDL was found predominantly in the medium (95%). Label from $^{125}$I-TC-LDL remained predominantly in the cells with only 6% escaping to the medium as TCA-soluble products. Total uptakes of [$^{125}$I-TC]-LDL and $^{131}$I-LDL were not different.

LDL was derivatized to varying extents with the TC ligand, and its ability to compete for uptake and catabolism of $^{125}$I-LDL by fibroblasts was compared to that of underivatized LDL. The presence of up to 17 residues of TC ligand per 625,000 daltons of LDL protein (the presumed molecular weight of Apo B in LDL) did not significantly alter the ability of LDL to compete with $^{125}$I-LDL in this receptor-mediated process.

Derivatization of proteins with the TC ligand also did not detectably alter their plasma decays in vivo. Human LDL derivatized with $^{125}$I-TC exhibited plasma decay kinetics similar to those of $^{131}$I-LDL. Similarly, the decay of $^{125}$I-TC-labeled rat apo Al in rats was indistinguishable from $^{131}$I-apo Al, and $^{125}$I-TC-labeled rabbit albumin decayed in rabbits like albumin directly iodinated with $^{131}$I.

The adequacy of trapping of the TC label was studied in vitro in terms of the uptake and retention of TC-LDL by cultured human fibroblasts. Fibroblast cells were exposed to 5–50 micrograms TC-LDL per ml. Leakage from fibroblasts of $^{125}$I-labeled catabolic products soluble in 10% trichloroacetic acid during 24 hr exposure of TC-LDL was only about 5.0 of the total $^{125}$I-TC-LDL uptake.

Experiments in vivo disclosed a similarly low rate of leakage (i.e. about 5% per day) from tissues. Asialofetuin, a protein targeted for rapid uptake by liver, was labeled with the $^{115}$I-TC ligand and intravenously injected into rats. Animals were killed either 1 hr. or 24 hrs. later and tissues were examined for $^{125}$I content. After 1 hr., the plasma was virtually cleared of $^{125}$I, with less than 5% of the injected dose remaining. Since [$^{125}$I-TC]-asialofetuin was nearly completely catabolized, total $^{125}$I in tissues was taken as a measure of catabolism by those tissues. After 1 hr., about 90% of the injected $^{125}$I was found in the liver. After 24 hrs., the liver still contained about 68 of the injected dose; the gut contents and feces contained about 25%, accounting for the loss from liver, presumably by biliary excretion. The rest of the tissues contained about 5% of injected label after 1 hr. and 5% after 24 hrs. Only 2.5% of injected $^{125}$I appeared in urine over 24 hrs. Thus, there was very little leakage of the TC label from liver except to bile, and $^{125}$I did not redistribute from liver to other tissues.

In studies of apo Al metabolism, reported in detail elsewhere (Glass, C. K., Pittman, R. C. and Steinberg, D. (1982) Submitted to J. Biol. Chem.) [$^{125}$I-TC]-apo Al was intravenously injected into rats and the tissues examined for $^{125}$I content 24 hrs. or 48 hrs. later. After 24 hrs., more than 90% of [$^{125}$I-TC]-apo Al had been irreversibly cleared, and again total label content of tissue was used as a measure of degradation. In this case no single organ predominated in catabolism of the protein. After 24 hrs. only about 6% of the labeled adduct was recovered in urine. After 48 hrs., the only tissues with $^{125}$I contents significantly different from their contents at 24 hrs. were liver (where a small decrease in label content was matched by a small rise in label in gut contents), and urine which increased to about 9%. Thus, there was an acceptably low leak rate, and again no evidence of label distribution.

The adequacy of trapping of the radiolabeled adduct was also studied using asialotransferrin, a protein targeted for uptake by both liver parenchymal cells and cells of bone marrow. Transferrin was labeled with the $^{125}$I-TC adduct and intravenously injected into rabbits. Three hours later the plasma was nearly cleared of $^{125}$I ($<10$% of injected remaining). At that time tissues were examined for $^{125}$I content; the label was found predominantly in liver and in bone marrow. At 24 hr. label was still found predominantly in liver and bone marrow. Here again there was an acceptably low rate of leakage (assuming label in gut contents and feces is attributable to liver), and no evidence for redistribution of label to other tissues.

In the examples above which examine the sites of degradation of asialofetuin, apo Al and asialotransferrin, the tissues were assayed at times after injection that were long compared to the plasma residence of the proteins. These times in all cases were at least 5 times the half-time for plasma clearance. Assuming a simple model for catabolism of plasma proteins, well over 90% of the protein had been catabolized in each case and little label remained in intact protein. However, this would not be true if proteins of less rapid catabolism are studied and tissues are examined at times after injection that are short relative to their plasma clearance rates. In those cases the presence in tissues of radiolabeled adduct attached to undegraded protein in trapped plasma and in intravascular spaces may contribute importantly to total radioactivity in tissues. When measurement of protein degradation is desired, this radioactivity is not necessary in proportion to degradation in any given tissue and will make a disproportionate contribution to total radioactivity in tissues of low catabolic activity. To resolve this problem, either the tissues must be examined at times after label injection that are long compared to the protein's plasma residence time, or the label in degradation products must be resolved from that in intact protein. The use of long experimental times must be balanced against the leak rates of products from tissues and, therefore, is not always feasible. Unfortunately, no simple, generally applicable method for physically separating degradation products from intact protein has been found. In the case of both the [$^{14}$C] sucrose and the *I-TC intracellularly trapped label, labeled degradation products accumulating in tissues remain for the most part attached to short peptides; these products are in part precipitated by trichloracetic acid and other common protein precipitants. Of course, gel filtration can be used to separate products and intact protein, but this is laborious when examining many tissues, and adsorption of catabolic products to cellular elements may pose a problem. In some cases special techniques may be applied to specific proteins, such as our use of an adsorption silica (Cabosil) to precipitate LDL in tissue homogenates of pigs (Pittman, R. C., Artie, A. D., Careu, T. E. and Steinberg, D. (1979) Proc. Natl. Acad. Sci. USA 76 5345, 5349).

An extension of the use of a radioiodinated, intracellularly trapped label as a radiological imaging agent involves the use of doubly-labeled targeted proteins. It has already been pointed out that the cellobiose-tyramine adduct is trapped in tissues on degradation of the protain to which it was covalently bound. In contrast, conventionally radioiodinated proteins (in which tyrosine moieties of the protein are directly iodinated) are degraded to yield radioiodinated catabolic products, predominantly iodotyrosine, which readily escape the cell. The iodotyrosine is quickly deiodinated, predominantly by the liver, to yield radioiodide. If a dose of iodide salt is given to act as a diluent of the radioiodide, the radioiodide is rapidly cleared by the kidneys and excreted in the urine. The net result is that at reasonably long times after injection of a conventionally radioiodinated protein, the label in the whole body and in individual tissues is predominantly in undegraded protein and little in catabolic products. Since the tissue content of the intracellularly trapped label represents both intact and degraded protein while the tissue content of conventional lable represents predominantly undegraded protein, the difference in content of the two labels represents catabolized protein.

This method has been tested in rabbits using low density lipoprotein and in rats using apolipoprotein A-I. In each case, the protein was labeled both with radioiodinated cellobiose-tyramine and by conventional radioiodination. $^{125}$I was used for one label and $^{131}$I for the other. The difference in label contents of tissues, corrected for the specific activity of each label in the intact protein, was a reasonable representation of the amount of protein degraded by those tissues.

A direct medical application of this method is in radiological imaging of target cells in man using presently available radiological scanning techniques. Another application lies in examining those target cells which take up the targeted protein at a rather slow rate, whether due to low intrinsic affinity of the cells for the targeted protein or due to slow appearance of the targeted protein in the pertinent extravascular pool to which the cells are exposed. Another application is in those cases where it is desired to view small clumps of target cells which do not bind a large absolute quantity of labeled protein and consequently do not show a good radiological image. In all these cases, the use of a conventional radio label, would yield a faint image against a high background. Use of the trapped label alone would magnify the image of the target cells since the difference between the target cells and the background would increase with time as the label accumulated in the cells and background decreased due to clearance of the labeled protein. Use of a conventional label on the targeted protein to instrumentally subtract out the background of undegraded protein would increase the sensitivity even more. Thus one obtains a dramatic increase in radiological sensitivity for target cells which exist in very small colonies, or cells which see the targeted protein gradually, or cells which have low affinity for the protein.

The principle of this double label approach is illustrated by experiments in vitro. A rabbit was injected with LDL labeled both with the $^{125}$I-TC ligand and by direct iodination with $^{131}$I. It was killed 24 hrs. later, and an homogenate prepared from the liver. This was subjected to gel filtration on 8% agarose. 89% of the $^{125}$I was retained beyond the void volume as degradation products. In contrast, $^{131}$I was found predominantly in the exclusion volume; $^{131}$I, therefore, traced mainly intact or nearly intact protein. When $^{131}$I in the exclusion volume was multiplied by the $^{125}$I/$^{131}$I ratio of the original doubly labeled LDL preparation and subtracted from the total $^{125}$I recovered from the column, it was calculated that only 9% of the $^{125}$I was accounted for in intact or nearly intact LDL. Therefore 91% of the $^{125}$I was calculated by this method to be degradation products, in good agreement with the 89% directly determined by retention of $^{125}$I on gel filtration. It is noteworthy that much of the $^{125}$I retained on 8% agarose was of molecular weight more than 1000, which represents the TC ligand still attached to short peptides. Only 66% of the $^{125}$I-labeled catabolic products retained by the gel column were soluble in 10% trichloroacetic acid.

To test the internal correction or double label approach in vivo, human LDL was directly iodinated with $^{131}$I and then labeled with the $^{125}$I-TC ligand. The resulting doubly labeled LDL ([$^{125}$I-TC], $^{131}$I-LDL) was injected into rabbits. Animals were killed 24 h later, and the tissues were examined for total $^{125}$I and $^{131}$I content and for their content of the two isotopes soluble and precipitable in 10% trichloroacetic acid.

Two ways of determining the amount of $^{125}$I in tissues as catabolic products of $^{125}$I-TC, $^{131}$I-LDL were compared. In method 1, pieces of tissue were directly radioassayed for total $^{125}$I and $^{131}$I content. The $^{125}$I content was corrected for the presence of undegraded [$^{125}$I-TC], $^{131}$I-LDL, assuming all $^{131}$I in the tissue was on intact $^{125}$I-TC, $^{131}$I-LDL. Thus, the tissue's $^{131}$I content, multiplied by the $^{125}$I/$^{131}$I ratio of the doubly labeled preparation, was subtracted from the total $^{125}$I content. In method 2, it was not assumed that $^{131}$I represented only undegraded protein. Rather, $^{131}$I precipitable in 10% trichloroacetic acid was used to correct the tissues' total $^{125}$I content for that still on undegraded protein to give a value for $^{125}$I present in degradation products.

It was found that agreement between the 2 methods was good for tissues of high and moderate specific activities. However, the least active tissues were underestimated by the first method. This may be explained in terms of the least active tissues' content of $^{131}$I that arose from catabolism of [$^{125}$I-TC], $^{131}$I-LDL in other tissues. Because of the size of the iodide pool and its approximately uniform distribution, all tissues carry a "background" of $^{131}$I-. In low uptake tissues, such as muscle, this may be large compared to the accumulation of $^{125}$I-labeled catabolic products. These tissues consequently may even display a negative value for $^{125}$I content corrected for intact protein using total $^{131}$I content. The over-correction occurs only in those tissues that contribute little to total protein degradation. Overall, catabolism of [$^{125}$I-TC], $^{131}$I-LDL will be underestimated only to the extent that $^{131}$I- or other $^{131}$I-labeled products from catabolism of the doubly labeled particles remains in tissues. In the experiments with LDL described above, the sum of the trichloroacetic acid-soluble $^{131}$I recovered in all tissues, corrected for the specific activities of $^{125}$I and $^{131}$I in the original LDL preparation, was equivalent to only 5% of the total $^{125}$I-labeled degradation products recovered in all tissues. Thus in this experiment the use of method 1 underestimated the catabolism of [$^{125}$I-TC], $^{131}$I-LDL overall by only 5% compared to method 2, and underestimation was apparent only in tissues of low activity and high mass. Thus even the first method, in which pieces of tissue are counted directly, is suitable for determining the overall pattern of protein degradation. Where careful evaluation of the least active tissues is needed, the more cumbersome but precise method 2 can be use.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein.

What is claimed is:

1. A method for intracellular trapping of a primary amine-containing therapeutic or tracer agent within a cell comprising the steps of:
   binding said agent to cellobiose to form a intracellularly trappable nonmetabolizable adduct;
   binding said adduct to a targeting agent to form a targeted adduct capable of introducing said adduct into said cell;
   introducing said targeted adduct into said cell wherein said agent remains attached to said cellobiose and is thereby trapped within said cell.

2. A method according to claim 1 wherein said therapeutic or tracer agent is bound to said cellobiose by reductive amination.

3. A method according to claim 2 wherein said agent is tyramine.

4. A method according to claim 2 wherein said agent is a primary amine chelating agent capable of carrying radio-metals.

5. A method according to claim 4 wherein said chelating agent is p-aminophenyl-ethylenedinitrilotetraacetic acid.

6. A method according to claim 3 wherein said tyramine is labeled with a radioisotope.

7. A method according to claim 2 wherein said agent is a compound enriched in $^{10}$B and containing a primary amino group.

8. A method according to claim 7 wherein said agent is 2-(p-aminophenyl)-1,2-dicarba-closo-dodecaborane which is enriched in $^{10}$B.

9. A method according to claim 1 wherein said targeting agent is selected from the group consisting of peptides, proteins antibiotics or glycoproteins.

10. A method according to claim 9 wherein said targeting agent is selected from the group consisting of antibodies, fragments or derivative products of antibodies, hormones and hormone analogues.

11. An intracellularly trappable adduct adapted to provide trapping of a therapeutic or tracer agent within cells comprising cellobiose having said agent bound thereto by a nonmetabolizable bond.

12. An adduct according to claim 11 wherein said agent includes a primary amine that is bound to cellobiose by reductive amination.

13. An adduct according to claim 12 wherein said agent is tyramine.

14. An adduct according to claim 12 wherein said agent is labeled with a radioisotope.

15. An adduct according to claim 12 wherein said agent is a chelating agent capable of carrying radio-metals.

16. An adduct according to claim 15 wherein said chelating agent is p-aminophenyl-ethylenedinitrilotitraacetic acid.

17. An adduct according to claim 11 wherein said agent is a compound rich in $^{10}B$ and containing a primary amino group.

18. An adduct according to claim 17 wherein said agent is 2-(p-aminophenyl)-1,2-dicarba-closo-dodecaborane.

19. A targeted adduct comprising the adduct according to claim 11 bound to a targeting agent.

20. A targeted adduct according to claim 19 wherein said targeting agent is a peptide, protein, glycoprotein or antibiotic.

21. A targeted adduct according to claim 20 wherein said targeting agent is an antibody fragment or derivative product of an antibody, hormone or hormone analog.

22. A targeted adduct according to claim 20 wherein said targeting agent is a protein chemically derivatized so as to cause it to be targeted.

23. A targeted adduct according to claim 22 wherein said targeting agent is selected from the group consisting of asialoglycoproteins, lactosylated proteins, acetylated and acetoacetylated proteins or maleylated proteins.

24. A targeted adduct according to claim 23 wherein said targeting agent is selected from the group consisting of asialofetuin, asialotransferrin, lactosylated low density lipoprotein, acetylated or acetoacetylated low density lipoprotein or maleyated albumin.

25. A targeted adduct according to claim 20 wherein said adduct includes radiolabeled tyramine.

26. A method for determining protein metabolism within cells comprising the steps of:
   introducing into the cells a targeted adduct according to claim 19, said targeted adduct including a protein metabolizable within said cells conjugated to said adduct as said targeting agent, said targeted adduct being labeled with a first radioisotope,
   simultaneously introducing into the cells said metabolizable protein labeled with a second radioisotope, said second radioisotope being removed from said cells naturally when the protein to which they are bound is metabolized, wherein the amount of second radioisotope remaining in tissues containing said cells is a measure of unmetabolized protein in said tissues;
   subtracting the amount of second radioisotope in said tissues from the amount of first radioisotope within said tissues to thereby determine the metabolism of said protein within said cells.

27. A method for radiological imaging of target cells comprising the steps of:
   exposing tissues to a targeted adduct according to claim 19 wherein said adduct is labeled with a first radioisotope and includes a targeted protein metabolizable within target cells of said tissues, said first radioisotope being trapped within said cells along with said adduct to thereby provide a measure of total protein introduced into said cells as well as protein in said tissue but not within cells, said method including;
   simultaneously exposing said tissues to said targeted protein labeled with a second radioisotope, said second radioisotope not being trapped in said cells, to thereby provide a measure of non-degraded protein within said tissues; and
   subtracting the measure of non-degraded protein provided by said second radioisotope from the measure of total protein provided by said first radioisotope to enhance the radiological imaging of said target cells.

* * * * *